United States Patent [19]

Nelson et al.

[11] 4,374,521

[45] Feb. 22, 1983

[54] SQUEEZE BAG TYPE RESUSCITATOR APPARATUS

[75] Inventors: Thomas W. Nelson, Lenexa, Kans.; Dennis L. Roehl, Kansas City, Mo.

[73] Assignee: Puritan-Bennett Corporation, Kansas City, Mo.

[21] Appl. No.: 186,643

[22] Filed: Sep. 12, 1980

[51] Int. Cl.³ .............................................. A61M 16/00
[52] U.S. Cl. ............................ 128/205.13; 128/204.26; 128/205.24; 137/102; 137/489; 137/113
[58] Field of Search ....................... 128/205.13, 205.17, 128/204.26, 204.27, 204.28, 203.28, 205.24; 137/102, 491, 113, 489

[56] References Cited

U.S. PATENT DOCUMENTS

| | | | |
|---|---|---|---|
| 1,270,565 | 6/1918 | Teter | 128/205.17 |
| 2,854,001 | 9/1958 | Humblet | 128/202.22 |
| 3,262,446 | 7/1966 | Stoner | 128/205.13 |
| 3,473,529 | 10/1969 | Wallace | 128/205.13 |
| 3,795,257 | 3/1974 | Fabish et al. | 137/491 |
| 4,054,133 | 10/1977 | Myers | 128/204.26 |
| 4,121,580 | 10/1978 | Fabish | 128/205.13 |
| 4,127,129 | 11/1978 | Cramer | 128/204.26 |
| 4,239,038 | 12/1980 | Holmes | 128/205.13 |

FOREIGN PATENT DOCUMENTS 1034384  7/1953  France ........................... 128/205.13

Primary Examiner—Henry J. Recla
Attorney, Agent, or Firm—Schmidt, Johnson, Hovey & Williams

[57] ABSTRACT

An improved overall arrangement is provided for resuscitators of the class adapted for administering substantially pure oxygen from a pressurized source thereof, and especially those of the kind functionally employing a demand responsive type oxygen supply valve in conjunction with a manually compressible squeeze bag. The demand type supply valve is mounted on and communicates with the end of the squeeze bag opposite from the end thereof on which the patient non-rebreathing valve (and the face mask associated with the latter) is mounted and communicates with the bag. In addtion to the operational and constructional advantages of the improved organization of the overall resuscitator apparatus, the construction and operation of various components thereof, including the demand type supply valve and the non-rebreathing valve, are individually improved in manner both contributing to better performance of the overall resuscitator apparatus and representing novel valving devices having potential utility even in other applications.

13 Claims, 15 Drawing Figures

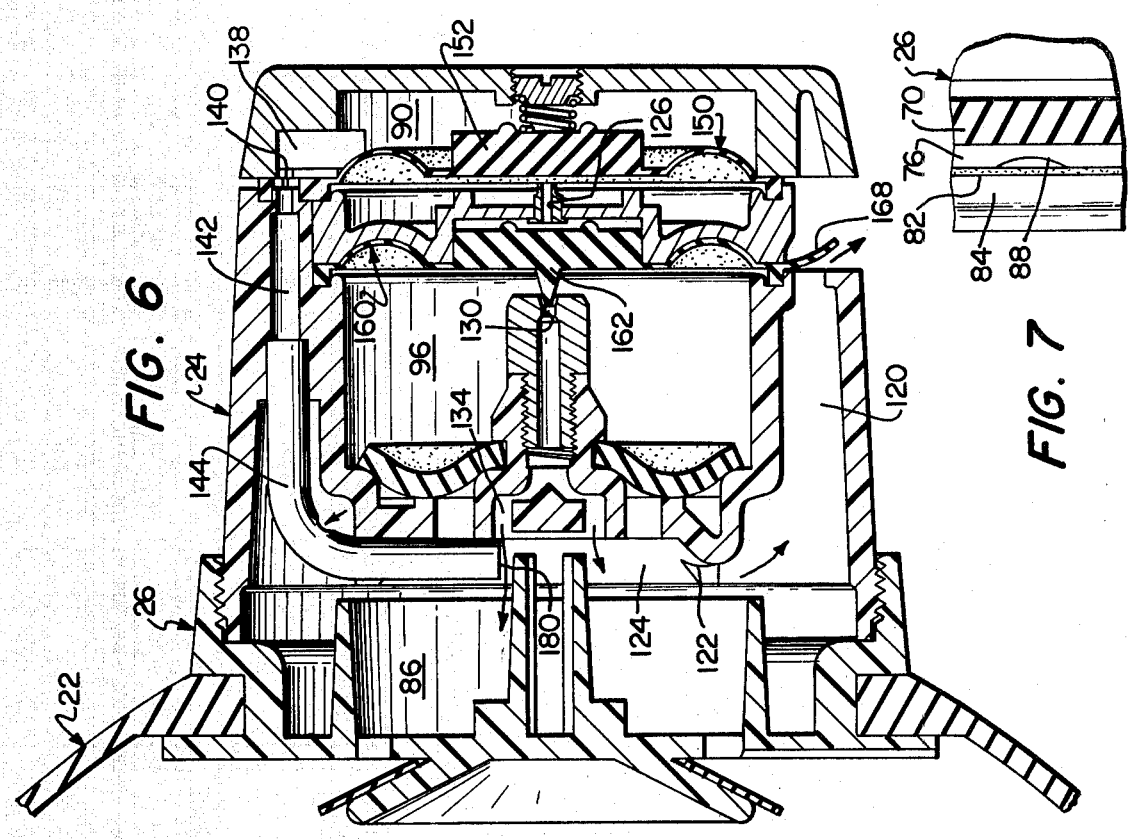
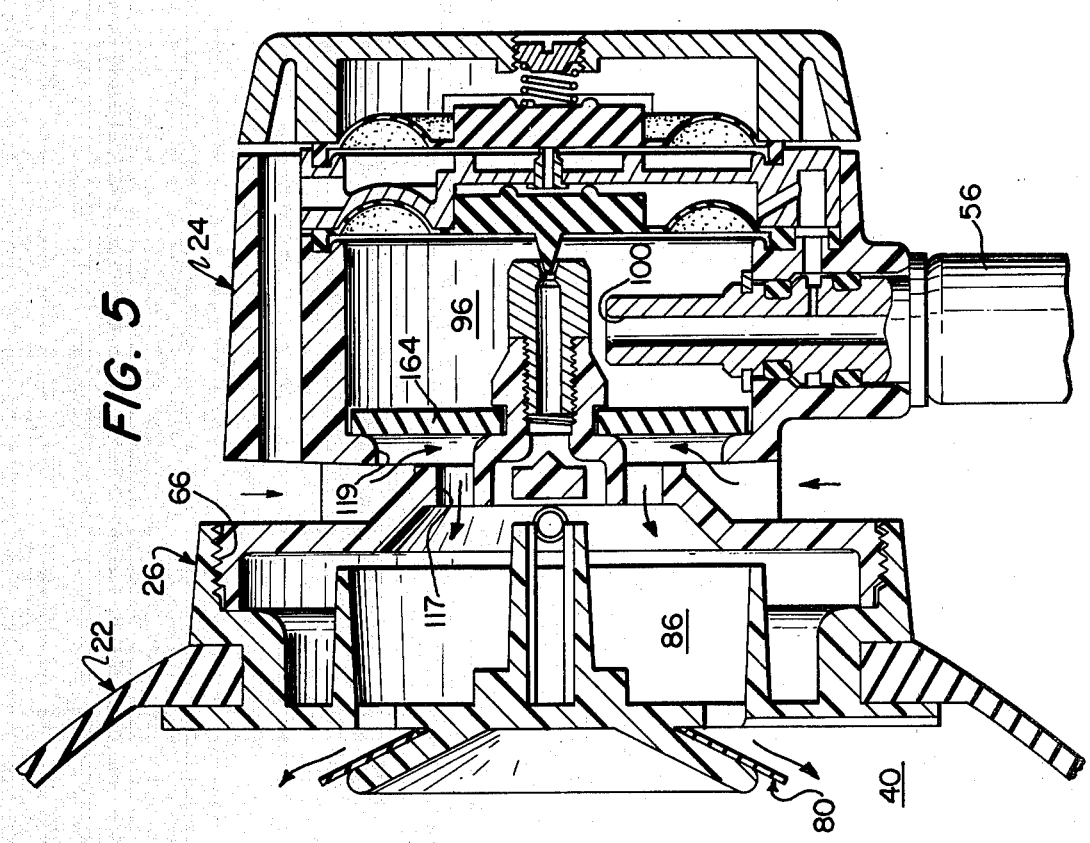

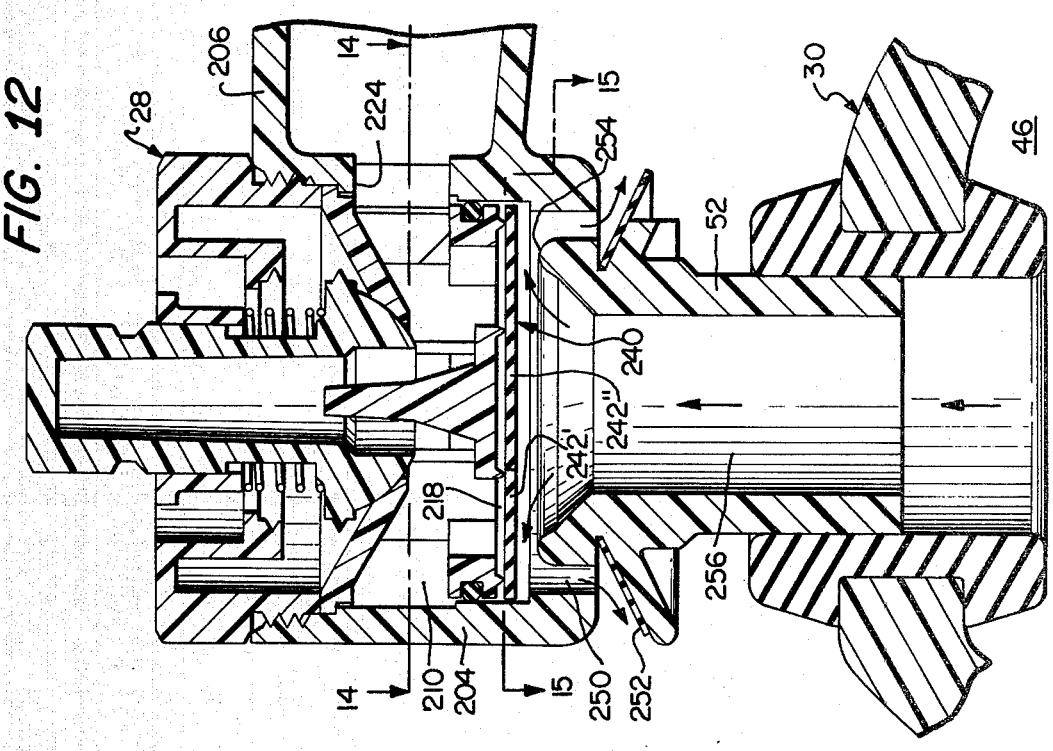
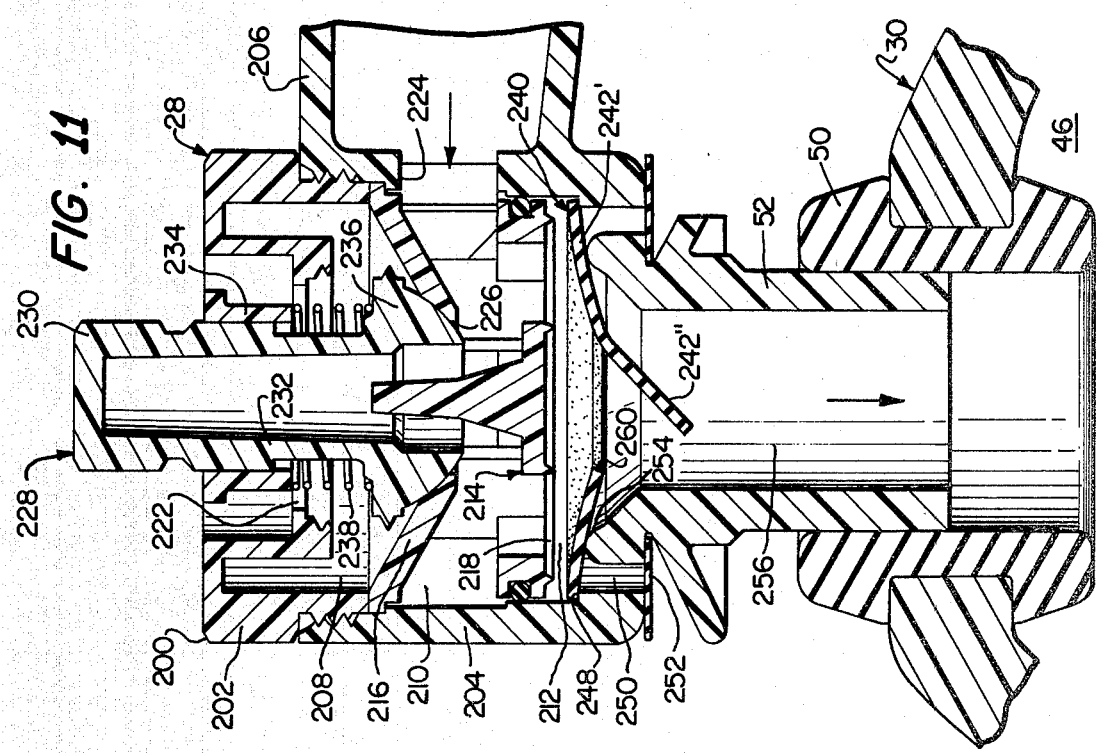

SQUEEZE BAG TYPE RESUSCITATOR APPARATUS

FIELD OF THE INVENTION

This invention relates to squeeze bag actuated resuscitator apparatus of the kind adapted to administer substantially pure oxygen obtained from a pressurized source thereof through a demand type oxygen supply valve whose operation is responsive to and controlled by differential pressures created by changing systemic conditions occurring during operation of the apparatus. The involved improvements pertain both to the overall resuscitator apparatus and to various individual components thereof, including the demand type oxygen supply valve and the patient non-breathing valve.

GENERAL BACKGROUND AND DESCRIPTION OF THE PRIOR ART

Resuscitation, as that term is herein used, refers generally to externally exerted efforts to assist or restore breathing of a patient whose natural breathing has either become impaired or has ceased, or to at least temporarily attempt to emulate the effects of more natural breathing in the patient, by forcing air or oxygen under appropriate pressure through the patient's natural airway system and into his lungs to inflate the latter at appropriate intervals separated by periods during which such application of air or oxygen under pressure is interrupted (an external physical pressure may be applied to the patient's chest) to permit the previously applied air to escape from the patient's lungs and the latter to deflate. A currently well known example is so-called "mouth-to-mouth resuscitation", in which the person administering the treatment blows air from his mouth into the mouth of the patient at rhythmic intervals and may alternately press on the patient's chest. In an environment where trained medical help is available, however, resuscitation has long normally been carried out with the assistance of various forms of resuscitator apparatus.

The forms of previous resuscitators of greatest interest as background for this invention, commonly called "squeeze bag" resuscitators, employed some type of manually compressible and self-restoring bag having the interior thereof fluid coupled to a face mask. In its most primitive conceptual form, such a device could be operated for resuscitation purposes simply by applying the mask to the face of a patient, manually squeezing the bag to force air from the bag through the mask and into the patient's lungs, releasing the squeezing pressure from the bag and removing the mask from the patient's face to permit escape of air from the patient's lungs at the same time the bag was restoring itself and thereby filling itself with fresh atmospheric air through the mask, perhaps retaining the bag in its restored condition until the time for the next bag squeezing operation, then repeating such cycle. Even in that crude form, it will be appreciated that the squeeze bag type of resuscitator offered a number of advantages as compared with other, more sophisticated types of machine powered, artificial breathing inducing equipment, including its adaptability to being portable because of its general simplicity and reliance for operating power upon merely the manual squeezing of the bag by the person administering the treatment, and its inherent characteristic of permitting a trained person administering treatment to directly control both the quantity of air forced into the patient's lungs and the intervals of doing so to best suit the size and condition of the patient through choice of the extent and timing of squeezing the bag.

Even relatively early squeeze bag resuscitators soon incorporated various refinements, including employment of resilient squeeze bags adapted to be conveniently held in one hand and to have the face mask carried more or less directly on the frontal extremity of the bag to increase portability and facilitate use by a single person, provision of a bag fill valve (an inward flow permitting check valve for communicating the interior of the bag with the atmosphere) to permit refilling of the bag with fresh air during its restoration phase without removing the mask from the face of the patient, and, in conjunction with the latter, provision of a patient non-rebreathing valve assembly interposed between the bag and the mask for in some manner permitting fresh air to move from the bag into the mask during the squeeze phase but venting air returned to the mask from the patient's lungs during the restoration or restored phases to atmosphere, rather than its passing into the bag from which it would be forced back into the patient's lungs or "rebreathed" during the next squeeze phase.

It should be noted in passing that the provision of a suitable non-rebreathing valve assembly is a non-trivial matter involving much more than merely a bag-to-mask flow permitting check valve and a mask-to-atmosphere flow permitting check valve, even to perform the basic function mentioned above, since such a pair of check valves alone would also vent to atmosphere air intended to be forced from the bag into the patient's lungs during the squeeze phase. This problem is significantly further complicated when attempt is made to safely and effectively also provide for accommodation to (rather than resistance to or suppression of) possible efforts of the patient to resume natural breathing, for protection of the patient against excessive pressures, etc. The result has been resort to a variety of types of of non-rebreathing valve assemblies of increasing complexity tending to reduce reliability, compound maintenance requirements, increase costs, and in general give rise to unnecessary practical problems for users, as well as of nature typically tending to involve compromised performance of one or more of the needed functions.

During the course of previous development of squeeze bag type resuscitators, it was recognized that it would be desirable in treating some patients to be able to administer oxygen, or at least oxygen enriched air, rather than just atmospheric air. Again, the problem was non-trivial and could not be solved merely by the continuous introduction of oxygen under pressure to the squeeze bag, since that would result in a pressure within the bag being more or less continuously communicated to the lungs of the patient through any patient non-rebreathing valve assembly adapted for performing its own primary functions, even during the restoration and restored phases of the bag cycle.

Accordingly, the development of practical means for introducing oxygen into the squeeze bag initially proceeded along lines of providing merely oxygen enrichment for the air drawn into the squeeze bag from the atmosphere during the restoration phase of the bag cycle, with the probably best (and still prevalent) approach to oxygen enrichment being to provide an elongate tube of relatively large diameter having one end thereof in fluid communication will the fill valve opening of the bag (typically at the extremity of the bag opposite from the non-rebreathing valve and mask) and the other end thereof exposed to the atmosphere, together with a considerably smaller tube extending into the larger tube and coupled with a pressurized oxygen source for continuously releasing oxygen into the air entering and accumulating within the larger tube from the atmosphere at a location typically adjacent the atmospheric side of the fill valve. Such devices are commonly called "oxygen accumulators" and are effective to introduce a mixture of air reasonably enriched with oxygen into the bag during the restoration phase of its cycle, without significantly increasing the pressure within the bag (since one end of the larger tube of the accumulator is in free communication with the atmosphere).

The advent of the oxygen accumulator did not, however, satisfy the need for being able to employ squeeze bag type resuscitators for administering substantially pure oxygen to patients under certain, relatively frequently occurring circumstances, such as various cardiac conditions. Since it has been recognized that oxygen under pressure can not be continuously introduced into the squeeze bag without defeating the other functions and essential characteristics of this type of resuscitator, known prior or concurrent development efforts of others are understood to have been or to be concentrated upon providing various valving arrangements for activating and interrupting the supply of pressurized oxygen into various parts of the resuscitator system. Such valving arrangements are intended to respond automatically to particular conditions or operating states of the resuscitator system, typically function in response to sensings of differential pressures, and are commonly referred to as "demand oxygen supply valves".

The only prior demand supply valve of which we are aware, however, was located at the front or mask end of the squeeze bag, adjacent to and in physically and functionally integrated association with the patient non-rebreathing valve, resulting im impairment of balance in the resuscitator itself, as well as impairment of needed visibility and clearance for the possible application of other medical instruments or procedures during use of the resuscitator. Moreover, the mentioned prior demand supply valve and all other demand supply valves known to now be in the process of development all involve constructions subject to various operational limitations or disadvantages involving their inability to respond rapidly, effectively, automatically and reliably to all of the diverse operating conditions that may be encountered in normal use of the resuscitator, their tendency to adversely affect operation of the closely adjacent or associated non-rebreathing valve or vice versa, or their complexity and resultant difficulty of correct disassembly and reassembly during servicing or the cleaning typically required after every use, etc.

In a very real sense, prior squeeze bag resuscitators employing demand type oxygen supply valves for administering substantially pure oxygen appear to have envolved in something of a "house that Jack built" fashion, in which additional structures have from time to time supply been added to what had existed before in an effort to add additional features recognized as desirable, but without wholly adequate correlation of individual components and their operations with either each other or the overall resuscitator apparatus. It is the purpose and, we believe, the achieved goal of this invention to provide an improved resuscitator apparatus of the mentioned type, in which at least all of the recognized limitations and disadvantages of prior devices of the same general type are eliminated through a novel and better organization and arrangement of the overall apparatus, as well as by specific improvements to the nature and construction of certain of the primary component assemblies employed in the apparatus.

SUMMARY OF THE INVENTION

The improved resuscitator apparatus provided by this invention involves, in addition to the more detailed constructional and operational advances hereinafter described and which can be fully explained and appreciated only in the context of such more detailed consideration, what we regard as more fundamental advances relating to improvement of the demand type oxygen supply valve assembly per se, improvement of the patient non-rebreathing valve assembly per se, and improvement of the overall arrangement and construction of the resuscitator apparatus through disposition of such valve assemblies adjacent to and in fluid communication with opposite extremities of the squeeze bag to enhance both the physical and pneumatic operational characteristics of the apparatus.

Such improvements are cooperatively related to each other and conjointly yield our preferred embodiment of the novel resuscitator apparatus contemplated and achieved by the invention.

BRIEF DESCRIPTION OF THE DRAWINGS

In the accompanying drawings:

FIG. 5 is a fragmentary, cross-sectional view longitudinally of the apparatus similar to FIG. 4, except showing the demand supply valve assembly in a still different condition thereof;

FIG. 6 is a fragmentary, cross-sectional view longitudinally of the apparatus taken on line 6—6 of FIG. 2, showing the demand supply valve assembly in still another condition thereof looking downwardly from a central, normally horizontal plane thereof;

FIG. 7 is a fragmentary, cross-sectional view longitudinally of the apparatus taken on line 7—7 of FIG. 3; showing certain details of the mounting of the demand supply valve assembly upon the squeeze bag;

FIG. 11 is a fragmentary, cross-sectional view longitudinally of the apparatus, showing the patient non-rebreathing valve assembly in one condition thereof looking laterally from a central, normally vertical plane thereof;

FIG. 12 is a fragmentary, cross-sectional view similar to FIG. 11, except showing the non-rebreathing valve assembly in a different condition thereof;

DESCRIPTION OF THE PREFERRED EMBODIMENT

Figure 1:
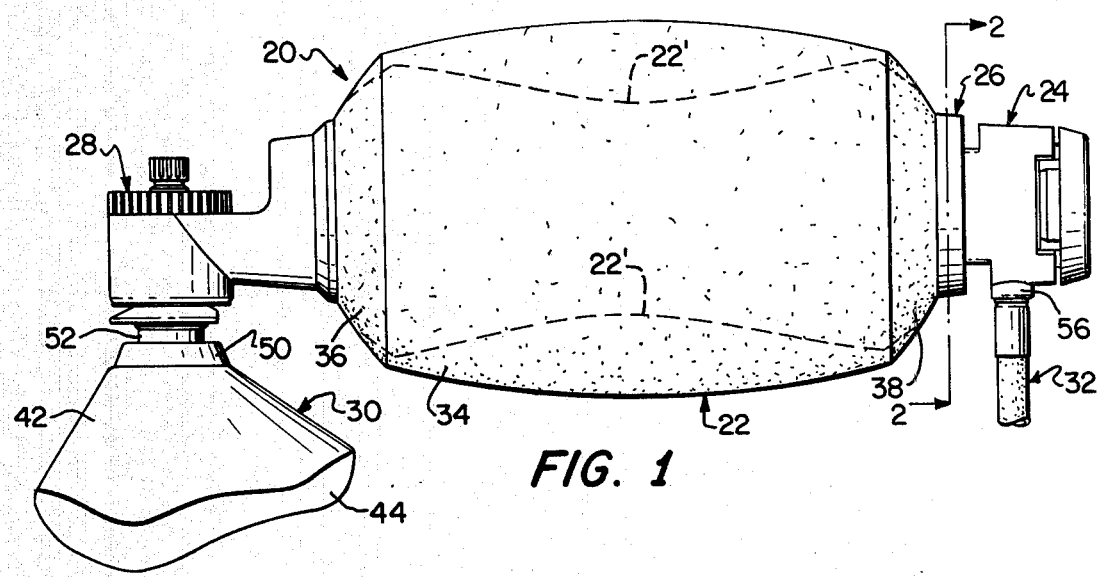
FIG. 1 is a side elevational view of our currently preferred embodiment of our improved resuscitator apparatus, with an illustrative, squeezed condition of the squeeze bag assembly thereof being indicated in dotted lines.

Referring initially to FIG. 1, our improved resuscitator apparatus 20 broadly includes a squeeze bag assembly 22, a demand type oxygen supply valve 24 mounted upon one end of the bag assembly 22 by a combined mounting and bag fill valve assembly 26, a patient non-rebreathing valve assembly 28 mounted upon the opposite end of the bag assembly 22, a face mask assembly 30 mounted upon the non-rebreathing valve assembly 28, and a conduit 32 for coupling the supply valve assembly 24 with a source of oxygen under pressure (not shown).

The bag assembly 22 is hollow, elongate with a generally oblate central section 34 and a pair of integral, generally frusto-conical end sections 36 and 38 each having a central opening 39 therethrough (see FIG. 3), manually compressible, resilient and self-restoring in shape, and preferably formed by molding from suitable synthetic resin plastic or rubber material. The apparatus 20 is intended to be held during use with the bag assembly 22 thereof in the hand of the user employing the same in administering oxygen to a patient for resuscitation purposes. The apparatus 20 is well balanced from front to rear and, when so held, can be conveniently manipulated by the user, both to position and retain the mask assembly 30 in proper engaging relationship with the face of a patient and to alternately exert squeezing pressure upon the bag assembly 22 and withdraw such pressure with such rapidity of action, to such extents and at such intervals as the user deems best suited for resuscitating the patient. When the bag assembly 22 is thus squeezed, the volume of the fluid chamber 40 (see FIG. 3) presented within the hollow interior of the bag assembly 22 is reduced and a corresponding quantity of oxygen is displaced from such chamber and forced under pressure through the non-rebreathing valve assembly 28 and the mask assembly 30 into the patient's airways and lungs. A compressed condition of the bag assembly 22 in response to squeezing thereof is generally indicated by the dotted lines 22' in FIG. 1. During squeezing of the bag assembly 22, the instantaneous pressure and rate of flow of oxygen to the patient are controlled by the rapidity of the squeezing action, the amount of oxygen applied to the patient is controlled by the extent to which the bag assembly 22 is compressed, and the timing of each application of oxygen to the patient coincides with the squeezing action and resultant compression of the bag assembly 22. When the user withdraws squeezing pressure from the bag assembly 22 to a force merely adequate for continuing to hold the apparatus 20, the bag assembly 22 will, by virtue of its resilient and self-restoring nature restore itself substantially to its normal shape as indicated in solid lines in FIG. 1 (or the user may choose to maintain a certain minimum squeezing pressure on the bag assembly 22 for more securely holding the apparatus 20, in which event the bag assembly 22 will restore itself to whatever extent is permitted by the user upon his withdrawal of a greater squeezing pressure previously applied to the bag assembly during an insufflation interval). In either case, during restoration of the bag assembly 22 to or toward its normal uncompressed shape, the volume of the interior chamber 40 therewithin increases and is refilled with oxygen from the demand supply valve assembly 24 through the fill valve assembly 26. The construction and operation of the supply valve assembly 24, the fill valve assembly 26 and the non-rebreathing valve assembly 28, as well as the effects of efforts of the patient to breath naturally and various other special conditions, will be discussed in greater detail hereinafter.

The face mask assembly 30 may be of any conventional character adapted to cover and communicate with the nose and mouth of the patient and to effect a reasonable pneumatic seal with the surrounding parts of the patient's face without the application of undue force for pressing the mask assembly 30 against the patient's face. Typically, the mask assembly 30 will include a main body 42 molded of synthetic resin plastic or rubber material having a contoured, softer, sealing rim 44 defining the larger open extremity of an internal cavity 46 (see FIG. 11) adapted to communicate with the patient's nose and mouth; a smaller open extremity 48 (see FIG. 11) of the cavity 46 is provided with resilient collar 50 (see FIG. 11) for firmly but removably mounting the mask assembly 30 upon a tubular conduit portion 52 of the non-rebreathing assembly 28 through which the latter is placed in fluid communication with the cavity 46 of the mask assembly 30.

The oxygen supply conduit 32 will be coupled with a tank or other suitable source of breathable oxygen (not shown), which typically should provide oxygen to the supply valve assembly 24 at a pressure of about 50 p.s.i.g. The conduit 32 is oppositely coupled to an oxygen inlet port 54 (see FIG. 3) by a fluid coupling assembly 56 further described hereinafter.

Figure 2:
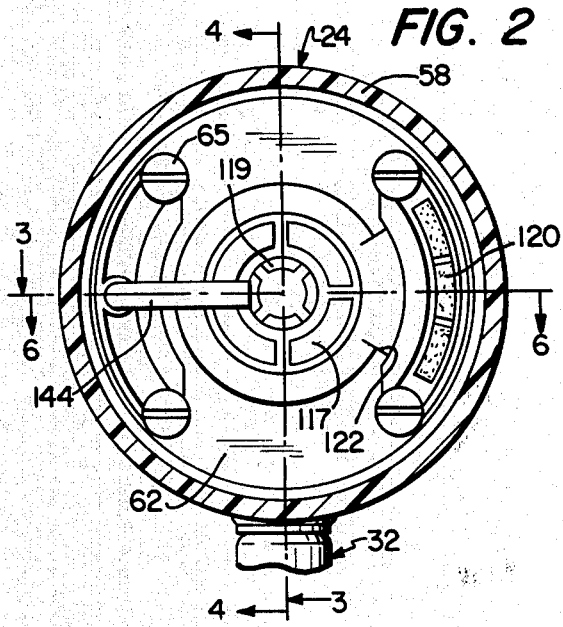
FIG. 2 is a cross-sectional view transversely of the apparatus taken on line 2—2 of FIG. 1, showing the demand oxygen supply valve assembly essentially in end elevation from the end thereof facing the squeeze bag assembly.
Figure 8:
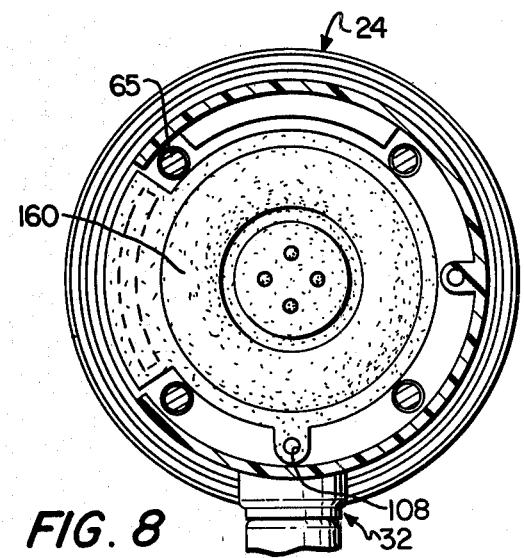
FIG. 8 is a cross-sectional view transversely of the apparatus taken on line 8—8 of FIG. 4, showing certain details of the demand supply valve assembly.
Figure 9:
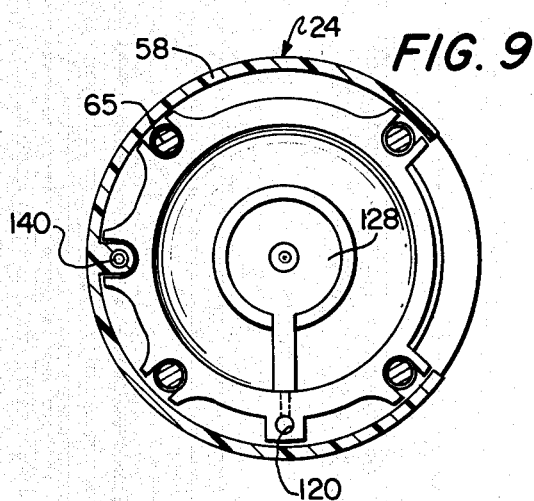
FIG. 9 is a cross-sectional view transversely of the apparatus taken on line 9—9 of FIG. 4, showing certain details of the demand supply valve assembly.
Figure 10:
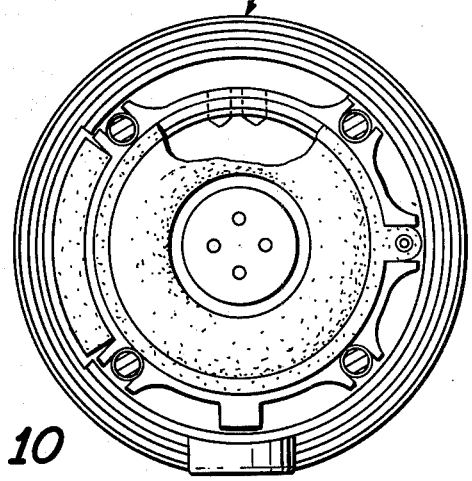
FIG. 10 is a cross-sectional view transversely of the apparatus taken on line 10—10 of FIG. 4, showing certain details of the demand supply valve assembly.
Figure 3:
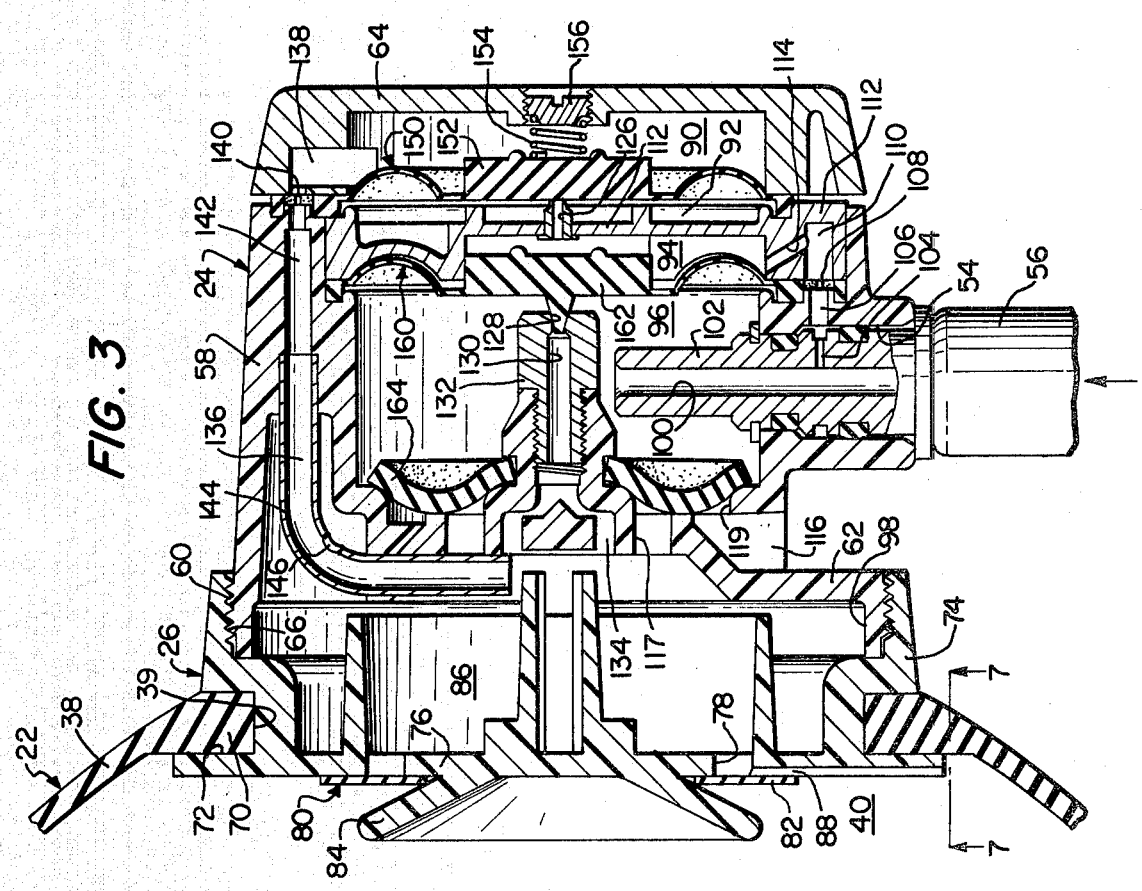
FIG. 3 is a fragmentary, cross-sectional view longitudinally of the apparatus taken on irregular line 3—3 of FIG. 2, showing the demand supply valve assembly in one condition thereof looking downwardly from a central, normally horizontal plane thereof as to the left half of FIG. 3 and looking laterally from a central, normally vertical plane thereof as to the right half of FIG. 3.
Figure 14:
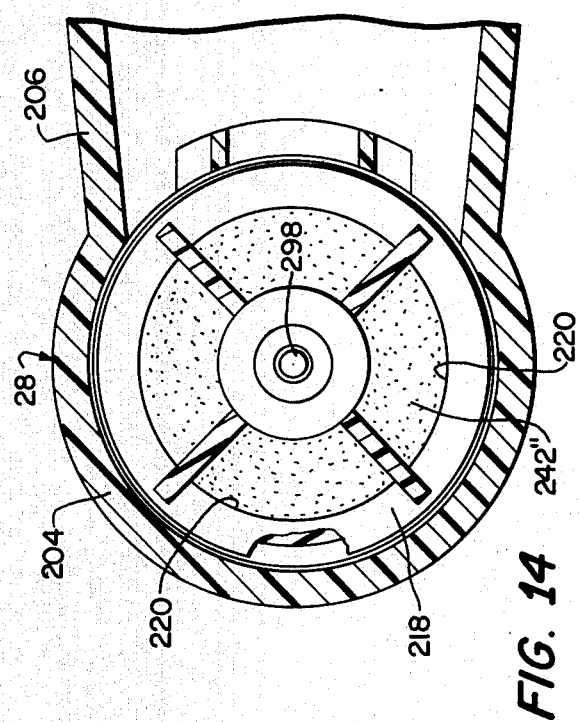
FIG. 14 is a fragmentary, cross-sectional view longitudinally of the apparatus taken on line 14—14 of FIG. 12, showing certain details of the non-rebreathing valve assembly.
Figure 15:
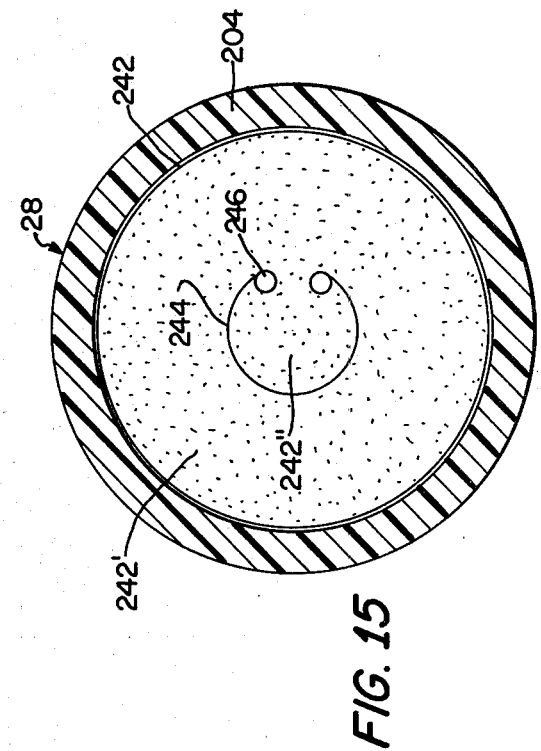
FIG. 15 is a fragmentary, cross-sectional view longitudinally of the apparatus taken on line 15—15 of FIG. 12, showing certain details of the non-rebreathing valve assembly.

Reference is next made generally to FIGS. 2–10 inclusive showing the mounting and fill valve assembly 26 and out improved demand type oxygen supply valve assembly 24 in greater detail, and initially to FIGS. 2 and 3 in particular, in the latter of which the supply valve assembly 24 is depicted in a condition thereof in which no oxygen is passing through the supply valve assembly 24 and the fill valve assembly 26 to the squeeze bag assembly 22. This condition will occur when the bag assembly 22 is in its standby state, that is, when it has been filled with oxygen during restoration to or toward its normal uncompressed condition after withdrawal of squeezing pressure following a previous squeezing thereof and is not in the process of being progressively squeezed again (or, incidentally, when it has been squeezed, is not in the process of being further squeezed, and has not yet had the squeezing pressure withdrawn therefrom). It may be helpful to broadly note at this stage that the demand supply valve assembly 24 operates to supply oxygen to the bag assembly 22 only when a negative pressure is presented within the chamber 40 of the bag assembly 22 with respect to the pressure of the oxygen supplied to the demand supply valve assembly 24, as will be further explained. It will also be assumed during initial description of the demand supply valve assembly 24 that the non-rebreathing valve assembly 28, to be later herein explained, is functioning in the general manner previously referred to, unless otherwise indicated.

The housing 74 of the mounting and bag fill valve assembly 26 may also be formed of synthetic resin material and includes a transverse end wall 76 adjacent the bag chamber 40, which is provided with apertures 78 therethrough. The bag fill valve 80 itself is provided by an annular, relatively flexible, synthetic resin or rubber, flapper valve member 82 positioned between the portion of the end wall 76 containing the apertures 78 and an annularly flared, integral retainer structure 84. As will be apparent, the bag fill valve 80 serves essentially as check valve for permitting relatively free fluid flow through the apertures 78 from a chamber 86 within the housing 74 and communicating with the partition 62 and other adjacent parts of the supply valve assembly 24 to the bag chamber 40, while preventing substantial fluid flow through the apertures 78 in the other direction from the bag chamber 40 to the chamber 86 of the assembly 26; thus, the fill valve 80 is, as previously noted, always closed except when the pressure in the chamber 40 is less than that in the chamber 86. It should be further observed, however, that a shallow groove 88 is formed in the end wall 76 and extends radially beneath the edge of the valve member 82 into communication with the bag side of one of the apertures 78 to provide a bleed path for a very limited fluid flow from the bag chamber 40 into the chamber 86 within the housing 74, even when the pressure within the former exceeds the pressure within the latter. The bleed path groove 88 is provided for the purpose of relieving or smoothing out possible, small, positive pressure spikes which may occur in the pressure of the oxygen within the bag chamber 40, such as due to inadvertent bumping of the bag assembly 22, and which, if they occur during the patient exhalation phase of operation, might otherwise "lock-out" the patient non-rebreathing valve assembly 28 from normal operation thereof, which in turn could present undesired resistance to an effort of the patient to exhale naturally, as will become clearer from the discussion of the non-rebreathing valve assembly 28 hereinafter.

The demand type oxygen supply valve assembly 24 includes a generally cylindrical housing 58 provided at one end thereof with external threads 60 and adjacent the same end thereof with an apertured, generally transverse partition 62, which may be integrally molded out of synthetic resin material, and a removable cap 64 conventionally secured in place at the opposite end of the housing 58 by bolt means 65 extending through the partition 62 and threaded into the cap 64. Cooperating pin and cavity means on the cap 64 and the adjacent end of the housing 58 assure proper positioning of the cap 64 on the housing 58. The housing 58 is removably secured on the mounting and bag fill valve assembly 26 by threaded coupling of the threads 60 on the assembly 24 with cooperating internal threads 68 on the assembly 26. The mounting and fill valve assembly 26 is in turn removably mounted on the end section 38 of the squeeze bag assembly 22, within the central opening 39 in the latter, through relatively tight, pneumatic reception of a portion 70 of the bag section 38 within a circumferential groove 72 of the housing 74 of the mounting and fill valve assembly 26.

Referring next especially to FIG. 3, wherein the oxygen-off or standby condition of the demand type oxygen supply valve assembly 24 is depicted, as evidenced by the closed condition of the bag fill valve 80 confirming that no substantial flow of oxygen (aside from a possible but insignificantly small amount through the bleed path groove 88) is occurring from the supply valve assembly 24 and the chamber 86 of the assembly 26 of the chamber 40 of the squeeze bag assembly 22, the following structural aspects of the supply valve assembly may be noted. The supply valve assembly 24 has internal fluid compartments or chambers 90, 92, 94 and 96 and an open end 98 communicating with the chamber 86 of the fill valve assembly 26. Passages or paths for possible fluid flow to and from the oxygen supply valve assembly 24 and between the chambers 90, 92, 94 and 96 thereof include a continuously open, main, oxygen supply inlet passage 100 from the oxygen supply conduit 56 to the interior of the chamber 96 through an extension 102 on the latter O-ring fitted into the supply port 54; a continuously open auxiliary supply pressure passage from the main supply inlet passage 100 through a lateral bore 104 in the extension 100, housing cavity 106, a small hole 108 in a tab on a flexible diaphragm subsequently described, a cavity 110 in a removable transverse partition structure 112 and a hole 114 in the structure 110 to the chamber 94; a valved passage 116 from the chamber 86 of the assembly via valved apertures 117 and 119 to atmosphere; a continuously open, vent passage 118 from the chamber 94 to atmosphere through housing cavities (see FIG. 4); a valved passage 120 from the open end 98 of the housing 58 communicating with the chamber 86 of the fill valve assembly 22 to atmosphere via a clearance 122 in a portion 124 of the partition 62 (see FIG. 6); a valved passage from the chamber 92 through a valve aperture 126 in the removable partition structure 112 to the chamber 94; a valved passage 128, 130 from the chamber 96 to the open end 98 of the supply valve assembly 22, via a cavity in a valve seat fitting 132 and housing cavities 134; a continuously open aspirator passage 136 from the chamber 90 to a position adjacent the ends of the apertures 134 communicating with the chamber 86 via a housing cavity 138; a small hole 140 in a peripheral tab of a diaphragm hereinafter identified; a housing cavity 142 and an aspirator tube 144; and a continuously open vent passage 146 between the aspirator tube 144 and the chamber 86 of the fill valve assembly 22 communicating with the open end 98 of the supply valve assembly 24. A flexible diaphragm 150 separates the chambers 90 and 92 and carries a valved member 152 that is normally biased into closing relationship with the passage 126 by a spring 154 whose tension can be adjusted with a screw plug 156 threadably mounted in the cap 64. Other than a possible part for fluid communication through the passage 126, the chamber 92 is separated from the chamber 94 by the partition structure 112. The chamber 94 is separated from the chamber 96 by a flexible diaphragm 160 carrying thereon a valved member 162 adapted for closing the passage 128. A flexible annular valve member 164 is mounted on the fitting 132 in disposition for closing the joint between apertures 117 and 119 and thereby the passage 116 from the chamber 86 of the fill valve assembly 122 to atmosphere. The passage 120 (see FIG. 6) is provided with a flexible, check valve member 168, which permits fluid flow only outwardly through the passage 120 to the atmosphere.

With the primary parts thus identified, further consideration may be given to the condition or disposition of various parts of the supply valve assembly 24 when the latter is in its standby or oxygen-off condition as depicted in FIG. 3. The oxygen entering the supply valve assembly via the passages 100 and 104 et seq. fill the chambers 96 and 94 respectively with oxygen at the supply pressure. The pressure within chamber 96 moves the valve member 164 into its closed position precluding atmospheric air from entering the chamber 86 via the passage 16 and the apertures 119 and 117. Chambers 96 and 94 are subjected to the same pressures on both sides of the diaphragm 160; however, there is a greater effective area of the diaphragm 160 in contact with the pressure within the chamber 94, which causes the valve member 162 to be held in closed relationship to the passage 128. Since in the condition of the assembly 24 under consideration there is no significant pressure within the chamber 90, by virtue of its communication with the un-pressurized chamber 86 via the aspirator tube 144, the spring 154 maintains the valve member 152 in closed relationship to the passage 126. In such condition, the chambers 90, 92 and 86 all remain substantially at atmospheric pressure, and the bag fill valve 80 will remain closed with the bag chamber 40 also substantially at atmospheric pressure. All of the mentioned chambers, of course, being filled with residual oxygen from the last previous bag restoration and filling phase of the operating cycle. In normal operation, the next phase of the cycle or operation of the apparatus 20 will typically involve squeezing of the bag assembly 22 to administer oxygen to the patient, during which the bag fill valve 80 will remain closed and the demand supply valve assembly 24 will remain in its standby or oxygen-off condition as just described, although it will be understood that the pressure of oxygen within the bag chamber 40 increases during squeezing of the bag assembly 22.

Figure 4:
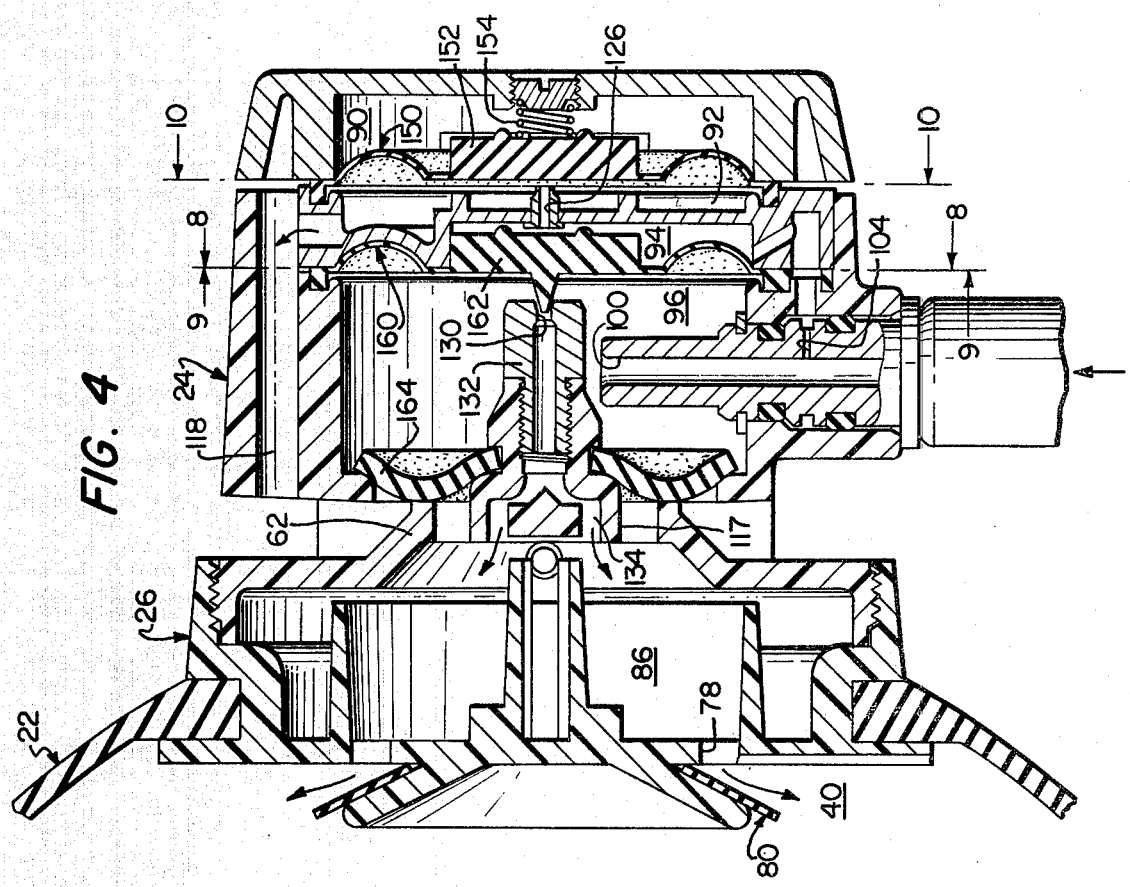
FIG. 4 is a fragmentary, cross-sectional view longitudinally of the apparatus taken on line 4—4 of FIG. 2, showing the demand supply valve assembly in a different condition thereof looking laterally from a central, normally vertical plane thereof.

Referring next more particularly to FIG. 4, the oxygen-on or bag filling condition of operation of the demand type oxygen supply valve 24 is illustrated. Such condition occurs either during restoration of the squeeze bag assembly 22 to its normal configuration after a release of squeezing pressure therefrom or during and in response to a spontaneous inhalation effort on the part of the patient. Suffice it to explain for the moment that, during spontaneous inhalation by the patient, the non-rebreathing valve asembly 28 will function to communicate the patient's demand for oxygen to the squeeze bag assembly 22 from which oxygen will be drawn to satisfy the patient's inhalation effort. It will further be understood, therefore, that either of the circumstances which will activate the oxygen-on or bag filling condition of operation involve the triggering event of lowered pressure within the chamber 40 of the bag assembly 22. Such reduced pressure within the bag chamber 40 opens the bag fill valve 80 and communicates the reduced pressure to the chamber 86 via the apertures 78. The same reduced pressure is also communicated from the chamber 86 to the adjacent face of the valve member 164 via the apertures 117 and to the chamber 90 via the vent 146 and the aspirator tube 144 (see FIG. 3). Accordingly, the pressure within chamber 92 will be greater than the pressure within chamber 90, which causes the diaphragm 150 to move against the bias of the spring 154 in a direction to shift the valve member 152 away from the passage 126 and thereby opening the latter. The oxygen within chamber 94 then vents to atmosphere via the opened valve passage 126 and the vent passage 118, which causes the pressure within the chamber 94 to drop by virtue of the fact that oxygen can not be replaced into the chamber 94 via the smaller passage 104 from the main oxygen supply passage 100 as fast as oxygen is escaping from the chamber 94 to atmosphere via the open valve passage 126, the supply pressure of oxygen within the chamber 96, therefore, will be greater than the pressure within the chamber 94, which causes the valve member 128 to shift away from the valve seat fitting 132 to open the passage 130, which in turn permits oxygen entering the passage 96 from the main supply passage 100 to pass through the valve passage 96 and the apertures 134 into the chamber 86 of the fill valve assembly 26, and thence through the aperture 78 and the open fill valve 80 into the cavity 40 of the bag assembly 22 for filling the latter. The last-mentioned action will continue as long as the bag assembly 22 is in its restoring phase expanding to its normal shaped configuration (or as long as spontaneous inhalation by the patient is drawing oxygen from the bag chamber 40).

Upon completion of the shape restoring and oxygen filling phase of the bag assembly 22 (or completion of the patient's spontaneous inhalation effort), the pressure within the bag chamber 40 will be restored to a level no longer less than the pressure within the chamber 86, and continued flow of oxygen from the chamber 96 into the chamber 86 and the chamber 90 will increase until the spring 154 will shift the diaphragm 150 and the valve member 152 carried by the latter to a position reclosing the passage 126. Closing of the passage 126 in turn causes the pressure to rise in the chamber 94 to a level such that the diaphragm 160 will shift its valve member 128 to reclose the passage 130, thereby stopping the flow of oxygen to the chamber 86 of the fill valve assembly 26 and to the bag chamber 40 of the squeeze bag assembly 22, whereupon the bag fill valve 80 will return to its normally closed position and the disposition and condition of the various parts of the demand supply valve assembly 24 will have been returned to essentially the same condition thereof as illustrated and explained in connection with FIG. 3, that is, to the oxygen-off or standby condition thereof.

Referring next to FIG. 5, there is illustrated a condition of the demand supply valve 24 in which it is adapted to respond to the oxygen supply from the conduit 56 via the main supply passage 100 being exhausted or the pressure thereof becoming too low for normal operation of the apparatus 20. Provision for such a contingency must be made for the sake of the patient's safety. In such event, the removal of normal oxygen pressure from the chamber 96 of the demand valve assembly 24 will cause the resilient valve member 164 to move away from the apertures 117 and 119, thereby placing the chamber 86 of the fill valve assembly 26 in direct communication with the atmosphere. Accordingly, the chamber 86 will remain continuously filled with air at atmospheric pressure, so that, upon the presentation of any lesser pressure within the bag chamber 40, as occurs during either bag shape restoration or spontaneous inhalation by the patient, the bag fill valve 80 will open to permit air from the chamber 86 to be drawn into the bag assembly 22 either for filling the latter or for withdrawal therefrom by the patient as required during spontaneous inhalation efforts. As is believed apparent, subsequent squeezing of the bag assembly 22 may then be resumed at the intervals desired for resuscitation purposes and will be entirely effective for administering breathable fluid to the patient, although such fluid will be air rather than oxygen after the oxygen supply has been depleted or cut off. During such subsequent squeezing phases of the operating cycle of the apparatus 20 in the absence of an adequate oxygen supply, the bag fill check valve 80 will, of course, close during each squeezing action, but the pathway for air from the atmosphere to the chamber 86 via the apertures 119 and 117 and the open valve member 64 will continue in the air passing condition thereof illustrated in FIG. 5 to maintain the chamber filled with available air.

Certain special aspects of the improved construction associated with the demand supply valve assembly 24 should next be noted. Those skilled in the art will appreciate that the removable mounting of the supply valve assembly 24 upon the fill valve assembly 26 will permit the apparatus 20 to remain functional for administering air to a patient in the event that the valve assembly 24 should somehow become damaged, simply by removing the same from the fill valve assembly 26, whereupon the bag fill valve 80 will permit the apparatus to be operated in essentially the fashion of older types of air resuscitator equipment. Similarly, if desired, the demand type oxygen supply valve assembly 24 may also be removed and a conventional oxygen accumulator device substituted therefor, if it should be desired to administer only oxygen enriched air rather than substantially pure oxygen to the patient; for such purpose it is preferred that the internal threads 66 upon the mounting and fill valve assembly 26 be made the same as those which will also accommodate available, oxygen accumulator devices. The improved demand type oxygen supply valve assembly 24 provided by this invention also involves additional special features of considerably greater subtlety and sophistication than the two special features just mentioned with regard to optional modes of possible operation of the apparatus 20. One of such special features addresses the problem arising from the fact that, whenever the demand type oxygen supply valve assembly 24 is actuated into its oxygen-on condition as illustrated and described in connection with FIG. 4, the pressure of the oxygen supplied to the bag assembly 22 must be sufficient to offset various pressure drops that will typically exist between the bag fill valve 80 and the mask assembly 30. If the pressure effectively supplied from the valve assembly 24 to the bag assembly 22 is inadequate, the shape restoration and bag filling phase of the operating cycle may be slowed to a degree affecting efficient overall operation of the apparatus 20. On the other hand, in the event that the oxygen pressure should rise to too high a level, the automatic operation of the oxygen supply valve assembly 24 could be accelerated to a degree causing pressure spikes to occur in the pressure of the oxygen within the bag assembly 22, which in turn could increase the resistance of the apparatus 20 to exhalation by the patient, or, if excessive, could cause "lock-out" or malfunctioning of the non-rebreathing valve assembly 28. FIG. 6 particularly illustrates features of the supply valve assembly 24 for solving the mentioned problem. In such regard, the aspirator tube 144 and its associated fluid flow paths 142, 140 and 138 previously described serves to enhance the operation of the improved oxygen supply valve assembly 24 during the on-oxygen condition of operation thereof in the following manner. A portion of the oxygen that passes through the passage 130 and the apertures 134 from the main oxygen chamber 96 flows at high velocity past the open end 180 of the aspirator tube 144 creating a suction or lowered pressure within the latter. Such lowered pressure thus created within the aspirator tube 144 and communicated to the chamber 90 is substantially less than the reduced pressure that would otherwise occur in the chamber 90 during on-oxygen operation as a result of the previously mentioned reduction of pressure therein resulting from the restoration phase of the bag assembly 22. By thus enhancing the pressure reduction within the chamber 90, the diaphragm 150 moves the valve member 152 even further away from the valve passage 126, which in turn also causes the diaphragm 160 to move the valve member 162 further away from the passage 130 to more widely open the latter. The result of these occurrences is a significantly increased rate of flow of supply oxygen from the chamber 96 through the valve passage 130 and into the chamber 86 of the fill valve assembly 26 than would otherwise occur in response to an initially reduced pressure within the chamber 86 resulting from shape restoration of the bag assembly 22 (or patient inhalation). Such advantage is achieved, however, only with the inherently attendant effect that the more drastically reduced pressure utilized in the chamber 90 causes it to take somewhat longer to subsequently increase the pressure within the chamber 90 to cause the diaphragm 150 to later move into position for closing of the passage 126 by the valve member 152 as previously described, which latter circumstance might tend to manifest itself as an undesired pressure spike in the pressure of oxygen in the chamber 86 and in the bag chamber 40 during the bag refilling phase of operation. It has been found, however, that recovery of the diaphragm 150 to shift the valve member 152 into closed relationship with the valve passage 126 may be sufficiently speeded up, even starting with a substantially reduced pressure in the chamber 90, to avoid or minimize the undesirable side effect that would otherwise occur from the pressure reducing action of the aspirator tube 144.

The check valve 168 upon the atmospheric vent passage 120, also shown in FIG. 6, may conveniently be constructed as an extension flap upon the diaphragm 160. The flap valve 168 will normally be closed when the pressure within the chamber 96 is reduced below atmospheric pressure during the filling phase of the operation of the squeeze bag assembly 22. However, if a pressure spike should occur within the chamber 86, either for the above discussed reasons or from any other cause, the flap valve 168 will open to bleed the increased pressure transient to the atmosphere and thereby smooth out any undesired variation of the pressure within the chamber 86. The flap valve 168 has an important additional function, however, in the event of a completely unexpected failure of the oxygen supply valve assembly 24 in which it would remain in its oxygen-on condition rather than normally returning to its standby condition after the bag filling phase of the operating cycle, it will be apparent that the pressure of oxygen within the chamber 86 could rise to a very high level limited only by the pressure of the oxygen being supplied to the valve assembly 24 from the supply conduit 56. Although such malfunction would not be anticipated, considerations of patient safety require that appropriate provision be made even for such remote contingency, since the failure condition described could tend to prevent exhalation or possibly even cause damage to his lungs. Accordingly, the provision of the resilient flap valve 168, which is designed to limit the maximum pressure within the chamber 86 to a safe level well below the "blow-off" level for the relief valve incorporated into the non-rebreathing valve assembly 28 and subsequently described.

Thus, it will be perceived that the improved demand type oxygen supply valve assembly 24 provided by this invention not only accomplishes all of the inherently essential functions of such a device in a straightforward and effective manner, but also incorporates special provisions both for improved operating characteristics and assuring the safety of the patient against types of possible malfunctions that might otherwise be dangerous.

Turning attention now to the patient non-rebreathing valve assembly 28, reference may be made generally to FIGS. 11–15 of the drawings, and particularly to FIG. 11 for purposes of initially identifying the primary parts involved. Our improved non-rebreathing valve assembly 28 includes a housing 200 having disassembleable, threadably joined upper and lower, generally cylindrical sections 202 and 204, which may be formed of molded, synthetic resin material, the lower section 204 of which includes an integral, tubular, lateral extension that is provided with a distal portion (not shown) preferably configured just as described for the bag mounted portion of the fill valve assembly 26 and illustrated in FIG. 3, including an external, annular groove (as at 72 in FIG. 3) for tightly but removably receiving an edge portion (as at 70 in FIG. 3) of the part of the bag section 36 surrounding the opening 39 at the front end of the bag assembly 22 opposite the end of the latter on which the fill valve assembly 26 and the supply valve assembly 24 are mounted. The tube 52 upon which the mask 30 is mounted also is preferably formed integrally with the lower housing section 204.

The non-rebreathing valve assembly 28 is internally provided with an upper compartment or chamber 208, a middle compartment or chamber 210, and a lower compartment or chamber 212. A cage assembly 214 is removably disposed within the housing 200 and provides an upper partition 216 provided with a central aperture between the upper and middle chambers 208 and 210 and a lower, webbed partition 218 provided with apertures 220 (see FIG. 14) between the middle and lower chambers 210 and 212. The upper chamber 208 normally is in communication with the atmosphere through the passages 222. The middle chamber 210 communicates through a port 224 and the tubular extension 206 with the opening 39 in the front end section 36 of the squeeze bag assembly 22. The middle chamber 210 can also communicate with the upper chamber 208 through the aperture 226, subject to the condition of a manually rotatable, pressure relief valve 228 having an exposed knob 230, an elongate stem portion 232 reciprocably mounted in a web-supported sleeve 234 of the upper housing section 202, and a valve member portion 236 normally urged downwardly by a spring 238 toward a position for closing the aperture 226. The middle chamber 210 can also communicate with the lower chamber 212 through the apertures 220 in the lower partition 218, subject to the condition of a compound, but simply fabricatable, valve assembly generally designated 240.

The compound valve 240 employs as its only moving part a reasonably flexible, somewhat resilient, normally flat, circular disc 242 (see also FIG. 15) having a concentric, arcuate cut 244 to divide the disc 242 into an annular, outer valve member portion 242' and an inner, flap-like valve member portion 242" effectively "hinged" to the outer portion 242' along a line of weakness extending between a pair of small holes 246 respectively adjacent the spaced ends of the cut 244. The disc 242 is supported at its periphery by resting upon an internal shoulder 248 of the lower housing section 204 at a level just below the lower chamber 212 and somewhat further below the apertured lower partition 218 of the cage 214. Underlying the outer portion 242' of the disc 242 are fluid passages 250 through the lower housing section 204, which are in the nature of vents to the atmosphere that are closable at their outer extremities by an annular, relatively flexible, flapper valve member 252 mounted on the tube 52 in a manner similar to the mounting of the bag fill valve member 82 on the bag side of the assembly 26 (see FIG. 3). Also underlying the outer portion 242' of the valve member 242 is an upwardly facing, annular, valve seat presenting end surface 254 of the tube 52, which communicates with the mask assembly 30 through the interior passage 256.

With the primary parts of the non-rebreathing valve assembly 228 thus identified, the operation thereof under various conditions may be considered. During the insufflation or bag squeezing phase of the operating cycle of the apparatus 20, the non-rebreathing valve assembly 28 will be in the condition illustrated in FIG. 11, which is effected in the following fashion. Squeezing of the bag assembly 22 exerts pressurized oxygen flow from the bag chamber 40, through the extension tube 206 and the port 224 into the middle chamber 210, and thence through the apertures 220 of the partition 218 into the chamber 212 in contact with the upper surface of both the outer and inner portions 242' and 242" of the valve disc member 242, thereby urging the outer disc portion 242' downwardly to close the exhalation vent passages 250 and the inner flap portion 242" swings downwardly to open an aperture 260 in the disc member 242 through which oxygen is passed into the passage 256 of the tube 52 and thence the mask assembly 30 for forced inhalation by the patient. Note that the arrangement of the compound valve assembly 240 assures that the user administering resuscitation with the apparatus 20 will retain control over the forced lung inflation phase of the operating cycle as long as the bag assembly 22 is being squeezed, which is desirable to prevent interference with needed rhythmic lung inflation operations by possibly aberrant, spontaneous efforts of the patient to exhale during that phase of the operating cycle.

In the event that the oxygen pressure within the middle chamber 210 should rise to an undesirable level, either during the bag squeezing or any other phase of the operating cycle, the excessive pressure thereby exerted on the bottom of the relief valve member 236 through the aperture 226 of the upper partition 216 of the cage 214 will cause the entire relief valve 228 to reciprocate upwardly against the bias of the spring 238, permitting the excessive pressure to escape from the middle chamber 210 through the aperture 226 into the upper chamber 208 and thence to the atmosphere through the vent passages 222. Once squeezing of the bag assembly 22 for a given lung inflating operation has been completed and squeezing force has been withdrawn from the bag assembly 22 to permit shape restoration and refilling of the latter, the decreased or negative pressure communicated to the middle chamber 210 during bag refilling will permit the disc member 240 to at least substantially resume its normal planar configuration, thereby opening a path of communication from the mask assembly 30 through the passage 256 of the tube 52 and thence between the lower surface of the disc member 242 and underlying valve seat 254, to the atmospheric vent passages 250. Moreover, completion of a lung inflation operation and the cessation of application of oxygen to the patient under pressure will normally be followed by the expulsion of gas from the patient's lungs, either through physical factors tending to exhaust pressure from the patient's lungs to an equilibrium level or through spontaneous or natural exhalation by the patient, which will exert a positive pressure from the mask assembly 30 through the tube passage 256 onto the lower surface of the disc member 242 that has already substantially returned to its normal, flat condition with its aperture 260 at least substantially closed. This is the condition of operation depicted in FIG. 12, from which it will be observed that the positive pressure of exhalation has caused the disc member 242 to rise off of the shoulder 248 and the outer portion 242' thereof to move into closing relationship to the apertures 220, thereby isolating the patient's exhalation gases from the middle chamber 210 and the bag assembly 22, as well as opening the previously noted exhalation path between the disc member 242 and the valve seat 254 to its maximum clearance. The same positive exhalation pressures, of course, opens the valve 252 over the vent passages 250 to permit free flow of the expelled gases to the atmosphere. Thus, the expelled gases are not passed into the bag assembly 22 or otherwise retained in any part of the apparatus 20 from which they could be readministered to or rebreathed by the patient. It should be observed that the non-rebreathing valve assembly 28 freely permits natural or spontaneous exhalation by the patient and discharges the expelled gases to atmosphere at any time during the operating cycle of the apparatus 20, except during intervals of controlled, force lung inflation in response to squeezing of the bag assembly 22 by the user as a part of the intended resuscitation treatment.

As will likely be apparent, but as should be understood, when the patient responds to the resuscitation effort as is the aim of the treatment by commencing spontaneous or natural breathing, however weak, the non-rebreathing valve assembly 28 will automatically accommodate to such circumstances. During such resumption by the patient of natural breathing, the non-rebreathing valve assembly 28 will function automatically in substantially the same manner as previously described in connection with FIGS. 11 and 12 for insufflation and exhalation during inhalation and exhalation respectively, with the exception that during natural inhalation the negative pressure created by the patient within the chamber 46 of the mask assembly 30, and the passage 256 of the tube 52 will be exerted upon the bottom surface of the valve member 240 and will serve to alter the condition of the latter to the state shown in FIG. 11, with the patient's own natural inhalation effort then drawing oxygen from the bag assembly 24 through the extension 206, the lower chamber 210 and the opened valve 240. Once natural breathing by the patient has commenced, the user will typically cease squeezing the bag assembly 24, but may desire to retain the resuscitator apparatus 20 in operative relationship with the patient for a further temporary period during which the patient may continue to breath substantially pure oxygen. The apparatus 20 still will permit the user to retain control over the resuscitation process, however, since, if the initial efforts of the patient to resume natural breathing are very weak or sporadic, the user can resume artificially induced lung inflation simply by squeezing the bag assembly 22 at appropriate intervals, between which the efforts of the patient to resume natural breathing will be encouraged by natural exhalation.

Figure 13:
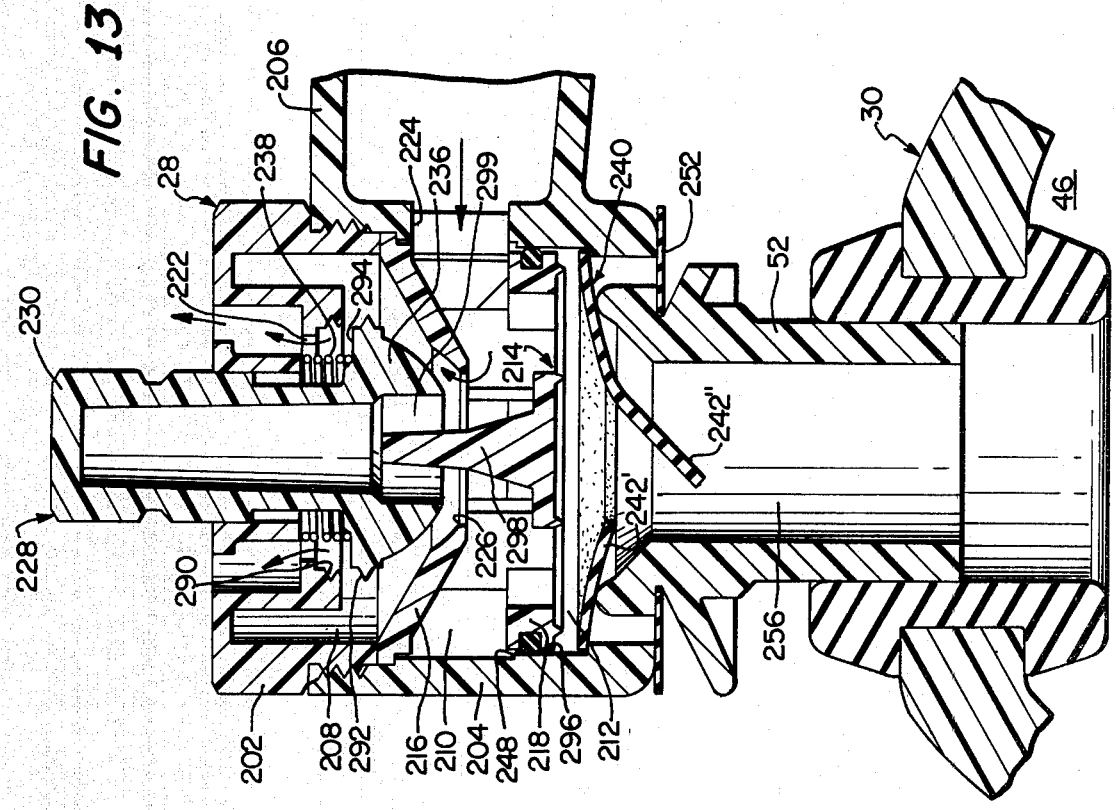
FIG. 13 is a fragmentary, cross-sectional view similar to FIG. 11, except showing the non-rebreathing valve assembly in a still different condition thereof.

Reference is next made to FIG. 13 for the purpose of considering certain special features of our improved non-rebreathing valve assembly 28 that are also believed to be advantageous and novel. One of such features is to provide means by which the user of the apparatus 20 can, under certain unusual circumstances so requiring, deactivate the normal, high pressure relief function of the non-rebreathing valve assembly 28. For that purpose, the upper housing section 202 and the pressure relief valve member 236 are respectively provided with cooperative, segmented threads 290 and 292. To thus disable the pressure relief valve 228 of the non-rebreathing valve assembly 28, it is merely necessary for the user to grasp the knob 230 of the relief valve assembly 228, lift the latter against the bias of the spring 238, and then twist the relief valve assembly 228 to interengage the segmented threads 290 and 292 for retaining the valve member 236 in a retained position in which its upper surface 294 will close the lower extremities of the vent passages 222 of the upper housing section 202. Such pressure relief disabling action can be done by the user very quickly, and, of course, the pressure relief function can be reenabled with equal speed and convenience merely by reversing the manipulation of the knob 230 to twist the valve assembly 228 to free the segmented threads 292 from the segmented threads 290, whereupon the biasing force of the spring 238 will immediately restore the valve member 236 to a position reclosing the relief valve passage 226 in the upper partition 216 and reopening the vent passages 222 in the upper housing section 202 for resumption of normal pressure relief functioning of the non-rebreathing valve assembly 28.

Another special feature of the construction of the non-rebreathing valve assembly 28, which is significant for both convenience and safety purposes, involves making such component with a minimum number of parts requiring disassembly for cleaning and sterilization between uses of the apparatus 20, with such parts being mutually so configured as to practically eliminate any chance for error in reassembly, such as reinsertion of parts in the wrong order or in a reversed orientation. Since cleaning and reassembly of the non-rebreathing valve assembly 28 may be carried out by persons less skilled than the trained user who employs the apparatus 20 for resuscitation purposes, anything which can reasonably be done to guard against incorrect reassembly of the non-rebreathing valve assembly 28 after cleaning thereof is important to assure that the apparatus 20 will be in proper condition for its next use under frequently emergency type circumstances. To such end, it will be observed that the parts of the non-rebreathing valve assembly 28 requiring disassembly for cleaning include only the upper housing section 202, the lower housing section 204, the cage 214 and the disc member 242'-242" of the valve 240. The valve disc member 242'-242" is, of course, reversible in character without effect upon its operation and, when dropped into the lower housing section 204, will naturally fall or be guided into place in its resting relationship upon the shoulder 248 of the lower housing section 204. The cage 214 combines various required internal structures of the valve assembly 28 into one convenient unit, and it will be noted that the diameter of the lower partition 218 thereof is somewhat less than the diameter of the upper partition 216 thereof; the inner diameter of the lower housing section 204 is similarly reduced at the zone 296 thereof which will normally receive the lower partition 218, so that the cage 214 can not be inserted into the lower housing section 204 in reversed condition. As a further safeguard against the last-mentioned possibility, the cage 214 includes an upstanding central projection 298 that normally extends into a cavity 299 in the bottom of the pressure relief valve member 236. Thus, proper reassembly of the non-rebreathing valve assembly 28 after cleaning thereof is both simplified and virtually assured by the construction provided.

Accordingly, it should be apparent that our improved construction for the resuscitator apparatus 20 and various components thereof not only accomplishes the major functions required from such apparatus, but do so in a particularly advantageous manner, as well as incorporating into apparatus 20 of the general kind involved additional advantages from the standpoints of both manufacture and functional operation. It should be equally apparent, however, that various minor and equivalent modifications from the preferred form of our improved resuscitator apparatus 20 disclosed herein for illustrative purposes could be employed without departing from the essence of our invention. It is to be understood, therefore, that our invention should be regarded as encompassing not only the subject matter literally defined by the claims which follow, but also mechanical equivalents thereof.

We claim:

1. In resuscitator apparatus:
    a manually distortable resilient, hollow squeeze bag assembly having a bag chamber therewithin whose volume varies with distortion thereof,
    said bag assembly being provided with a pair of separate openings respectively adjacent opposite extremities thereof and in communication with said bag chamber;
    a non-rebreathing valve assembly mounted on said bag assembly adjacent one of said extremities of the latter and having a first fluid port in communication with said bag chamber through one of said bag openings and a second fluid port;
    a patient interfacing assembly in communication with said second port of said non-rebreathing valve assembly; and
    a demand type oxygen supply valve assembly mounted on said bag assembly adjacent the other of said extremities of the latter and having an oxygen inlet adapted for connection with a source of oxygen under pressure, and an oxygen outlet arranged to communicate with said bag chamber through the other of said bag openings, said supply valve assembly including
    housing structure having a hollow interior, a fluid inlet port adapted for coupling with a source of oxygen under pressure, a fluid outlet port adapted for communicating with an outlet chamber subject to fluid pressure variation therewithin in response to the withdrawal of fluid therefrom, and first and second atmospheric vent ports for communicating with the exterior of said housing structure;
    means including a partition and a pair of differential pressure responsive diaphragms dividing the interior of said housing structure into a plurality of internal chambers,
    one of said diaphragms being between the first and second of said internal chambers,
    said partition being between the second and third of said internal chambers,
    the other of said diaphragms being between the third and fourth of said internal chambers,
    said inlet port being in continuous communication with said fourth internal chamber;
    first valve means including a valve member carried by said one diaphragm and a valve passage through said partition for selectively placing said second internal chamber in fluid communication with said third internal chamber;
    second valve means including a valve member carried by the other of said diaphragms and a valve passage through said housing structure for selectively placing said fourth internal chamber in fluid communication with said outlet chamber;
    a fluid passage within said housing structure for placing said first internal chamber in fluid communication with said outlet chamber;
    a fluid passage within said housing structure for placing said second internal chamber in fluid communication with said first vent port;
    a fluid passage within said housing structure for placing said outlet chamber in fluid communication with said second vent port; and
    differential pressure responsive valve means oppositely communicating with said fourth internal chamber and said outlet chamber, also oppositely communicating with said fourth internal chamber and said second vent port, responsive to a positive pressure of at least a predetermined level within said fourth internal chamber for normally closing said passage between said outlet chamber and said second vent port, and responsive to a pressure of less than said predetermined level within said fourth internal chamber for opening said passage between said outlet chamber and said second vent port.

2. In resuscitator apparatus as set forth in claim 1, wherein:
    said fluid passage for placing said first internal chamber in fluid communication with said outlet chamber includes an aspirator tube having one open end thereof disposed adjacent the path of fluid flow through said valve passage from said fourth internal chamber to said outlet chamber.

3. In resuscitator apparatus as set forth in claim 1, wherein:
    there is provided yieldable biasing means for urging said first valve means toward its closed condition.

4. In resuscitator apparatus as set forth in claim 1, wherein said non-rebreathing valve assembly includes:
    housing means having a hollow interior and a plurality of fluid ports for communicating said interior thereof with the exterior thereof;

partition means within said housing means and having a hole therethrough for dividing the interior of the latter into a plurality of fluid compartments, including a first compartment adapted to communicate with said squeeze bag assembly through the first of said ports of said housing means, and a second compartment adapted to communicate with said first compartment through said hole in said partition means, with said patient interfacing assembly through a second of said ports of said housing means, and with the atmosphere through a third of said ports of said housing means; and shiftable valve means responsive to differences in fluid pressure between said first compartment and said interfacing assembly for opening said hole and a path from said second compartment to said interfacing assembly through said second port of said housing means and closing said third port of said housing means when the fluid pressure in said first compartment is greater than the fluid pressure in said interfacing assembly, and for closing said hole and opening a path between said second and third ports of said housing means when the fluid pressure in said first compartment is less than the fluid pressure in said interfacing assembly.

5. In resuscitator apparatus as set forth in claim 4, wherein:

said shiftable valve means is disposed within said second compartment and comprises a deformable disc having a first portion shiftable between positions for alternately closing either said hole or said third port of said housing means, and a second portion shiftable between positions for alternately opening or closing a valve opening in said disc for respectively communicating or substantially blocking communication between a part of said second compartment in communication with said hole and said second port of said housing means.

6. In resuscitator apparatus as set forth in claim 5, wherein:

said disc of said shiftable valve means is floatingly received within said second compartment, and said hole is disposed adjacent one side of said disc, while said second and third ports of said housing means are disposed adjacent the other side of said disc.

7. In resuscitator apparatus as set forth in claim 4, wherein:

said housing means includes disassembleable sections, and said partition means and said shiftable valve means are freely removable from said housing means for cleaning when the sections of said housing are disassembled.

8. In resuscitator apparatus as set forth in claim 4, wherein:

there is partition structure providing a third compartment within the interior of said housing means, said third compartment being adapted for fluid communication with said first compartment through a pressure relief opening in said partition structure and with the atmosphere through a fourth of said ports of said housing means, there being a pressure relief valve assembly shiftably mounted on said housing means and yieldably biased toward a position thereof for normally closing said pressure relief opening in said partition structure.

9. In resuscitator apparatus as set forth in claim 8, wherein:

said pressure relief valve assembly is reciprocably and rotatably mounted on said housing means and includes a manual knob portion accessible exteriorly of said housing means, and said housing means and said pressure relief valve means are provided with cooperative, segmented thread means for selectively retaining said pressure relief valve means in a position thereof for closing said fourth port.

10. In resuscitator apparatus as set forth in claim 1, wherein said supply valve assembly includes:

a further vent passage in communication with said outlet and adapted for oppositely communicating with the atmosphere, and further normally closed valve means operably associated with said further vent passage and adapted to open to communicate said outlet with the atmosphere in response to an increase of at least a predetermined magnitude in the pressure within said further vent passage between said outlet and said further normally closed valve means.

11. In a demand type oxygen supply valve assembly for use in resuscitator apparatus or the like:

housing structure having a hollow interior, a fluid inlet port adapted for coupling with a source of oxygen under pressure, an outlet chamber a fluid outlet port communicating with said outlet chamber subject to fluid pressure variation therewithin in response to the withdrawal of fluid therefrom, and first and second atmospheric vent ports for communicating with the exterior of said housing structure;

means including a partition and a pair of differential pressure responsive diaphragms dividing the interior of said housing structure into a plurality of internal chambers, one of said diaphragms being between the first and second of said internal chambers, said partition being between the second and third of said internal chambers, the other of said diaphragms being between the third and fourth of said internal chambers, said inlet port being in continuous communication with said fourth internal chamber;

first valve means including a valve member carried by said one diaphragm and a valve passage through said partition for selectively placing said second internal chamber in fluid communication with said third internal chamber;

second valve means including a valve member carried by the other of said diaphragms and a valve passage communicating with said outlet port through said housing structure for selectively placing said fourth internal chamber in fluid communication with said outlet chamber;

a fluid passage within said housing structure for placing said first internal chamber in fluid communication with said outlet chamber;

a fluid passage within said housing structure for placing said second internal chamber in fluid communication with said first vent port;

a fluid passage within said housing structure for placing said outlet chamber in fluid communication with said second vent port; and differential pressure responsive valve means oppositely communicating with said fourth internal chamber and said outlet chamber, also oppositely communicating with said fourth internal chamber and said second vent port, responsive to a positive pressure of at least a predetermined level within said fourth internal chamber for normally closing said passage between said outlet chamber and said second vent port, and responsive to a pressure of less than said predetermined level within said fourth internal chamber for opening said passage between said outlet chamber and said second vent port.

12. In a demand type oxygen supply valve assembly as set forth in claim 11, wherein:
said fluid passage for placing said first internal chamber in fluid communication with said outlet chamber includes an aspirator tube having one open end thereof disposed adjacent the path of fluid flow through said valve passage from said fourth internal chamber to said outlet chamber.

13. In a demand type oxygen supply valve assembly as set forth in claim 11, wherein:
there is provided yieldable biasing means for urging said first valve means toward its closed condition.

* * * * *